United States Patent [19]
Hachiya et al.

[11] Patent Number: 6,150,566
[45] Date of Patent: Nov. 21, 2000

[54] SEPARATION AND PURIFICATION METHOD OF XYLENOL ISOMER

[75] Inventors: Tetsuo Hachiya; Seiji Aoki, both of Tokyo, Japan

[73] Assignee: ADCHEMCO Corporation, Tokyo, Japan

[21] Appl. No.: 09/271,433

[22] Filed: Mar. 18, 1999

[30] Foreign Application Priority Data

Mar. 20, 1998 [JP] Japan ................................. 10-072751

[51] Int. Cl.⁷ ................................................. C07C 37/68
[52] U.S. Cl. .............................................................. 568/750
[58] Field of Search ............................................. 568/750

[56] References Cited

U.S. PATENT DOCUMENTS

| | | | |
|---|---|---|---|
| 2,456,581 | 12/1948 | Cislak | 568/750 |
| 2,456,582 | 12/1948 | Cislak | 568/750 |
| 4,447,658 | 5/1984 | Leston . | |
| 4,499,312 | 2/1985 | Leston . | |

*Primary Examiner*—Michael L. Shippen
*Attorney, Agent, or Firm*—Oblon, Spivak, McClelland, Maier & Neustadt, P.C.

[57] ABSTRACT

At least one xylenol isomer can be separated and purified from a mixture, which contains the specific xylenol isomer and at least one organic substance other than the specific xylenol isomer, by bringing the mixture into contact with 1,1-di(4-hydroxyphenyl)cyclohexane as a host compound to form a complex of the specific xylenol isomer as a guest compound with the host compound and then having the specific xylenol isomer released from the complex. The mixture may contain at least two xylenol isomers consisting of 2,4-xylenol and 2,5-xylenol, and at least one of the xylenol isomers can be separated and purified by having it released from its complex with the host compound.

10 Claims, 1 Drawing Sheet

SEPARATION AND PURIFICATION METHOD OF XYLENOL ISOMER

BACKGROUND OF THE INVENTION a) Field of the Invention

This invention relates to a method for the separation and purification of at least one xylenol isomer useful as intermediates for medicines and agricultural chemicals, and more specifically to a method for the separation and purification of at least one xylenol isomer from a mixture containing the specific xylenol isomer along with at least one organic substance other than the specific xylenol isomer, which comprises using 1,1-di(4-hydroxyphenyl)cyclohexane as a host compound capable of selectively forming a host-guest complex (hereinafter simply called "a complex") with the specific xylenol isomer as a guest compound.

b) Description of the Related Art

For the separation and purification of at least one specific xylenol isomer from a mixture containing the specific xylenol isomer along with one or more xylenol isomers other than the specific xylenol isomer and/or one or more non-xylenol organic substances, a variety of methods are known, including, for example, simple purification of a specific xylenol isomer by recrystallization, separation of 2,5-xylenol from a mixture of 2,4-xylenol and 2,5-xylenol by a selective reaction of 2,5-xylenol with an aldehyde as disclosed in JP 64-3136 and JP 01-22832, separation of xylenol isomers from each other by adsorptive separation as disclosed in JP 08-268942, and selective recovery of 2,4-xylenol by the formation of a complex between 2,4-xylenol and a diamine compound as disclosed in JP 64-3137.

The separation by simple recrystallization can hardly separate and purify 2,4-xylenol which is low in crystallinity, although it permits separation and purification in the case of 2,5-xylenol which is high in crystallinity. Further, occurrence of microcrystals by recrystallization makes it difficult to perform filtration on an industrial scale. A further problem associated with this method is that the resulting product is not sufficient in purity.

The method, which makes use of a selective reaction between an aldehyde and a specific xylenol isomer, is applicable only for the purification of 2,4-xylenol. A problem associated with this method is that 2,5-xylenol is lost as a byproduct through its reaction with the aldehyde.

The adsorptive selection allows recovery of individual isomers. This method however involves a problem in that, for its industrial application, namely, for chromatographic fractionation or for separation and purification by a simulated moving bed permitting the chromatographic fractionation in a continuous manner, complex and costly, special facilities are needed, resulting in the need for a substantial initial cost.

Further, the method making use of the formation of a complex with a diamine permits separation and purification of 2,4-xylenol which forms a complex with the diamine compound, but can hardly separate and purify the other xylenol isomers. Another problem associated with this method resides in that it must use the diamine compound which is highly toxic.

SUMMARY OF THE INVENTION

An object of the present invention is therefore to solve the above-described problems of the conventional art and to provide a method for separating and purifying a specific xylenol isomer with high purity by simple procedures.

Interested in the separation and purification method making use of a complex known as a separation technique for phenol compounds, the present inventors have proceeded with an extensive investigation. As a result, it has been found that 1,1-di(4-hydroxyphenyl)cyclohexane selectively includes a xylenol isomer depending on its concentration, leading to the completion of the present invention.

To achieve the above-described object, the present invention provides a method for the separation and purification of at least one specific xylenol isomer from a mixture comprising the specific xylenol isomer and at least one organic substance other than the specific xylenol isomer, which comprises bringing the mixture into contact with 1,1-di(4-hydroxyphenyl)cyclohexane as a host compound to form a complex of the specific xylenol isomer as a guest compound with the host compound, and then having the specific xylenol isomer released from the complex.

According to the method of the present invention, the specific xylenol isomer can be readily recovered with high purity from the mixture containing the specific xylenol isomer along with the organic substance other than the specific xylenol isomer.

DETAILED DESCRIPTION OF THE INVENTION AND PREFERRED EMBODIMENTS

Figure 1:
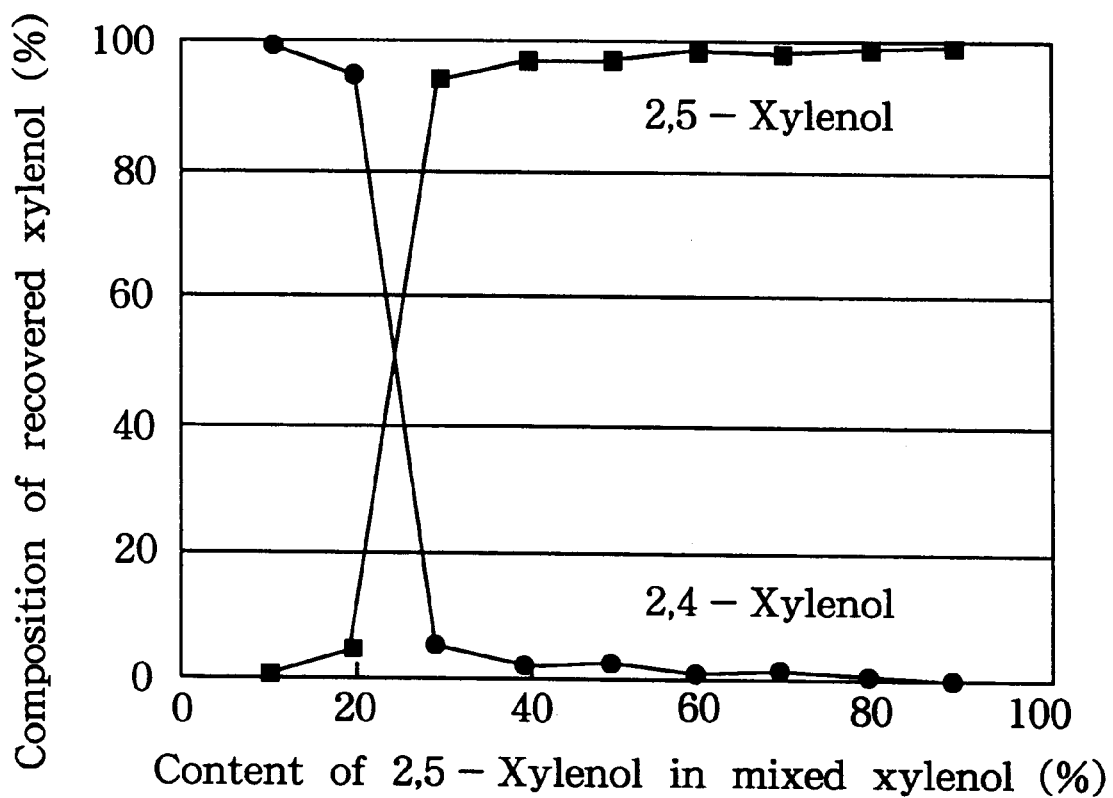
FIG. 1 is a graph showing a relationship between the contents of 2,5-xylenol in mixed xylenols employed in Examples 7–15 of the present invention and the compositions of xylenols recovered there.

The present invention will hereinafter be described in further detail on the basis of preferred embodiments.

The mixture comprising at least one xylenol isomer and at least one organic substance other than the specific xylenol isomer, to which the present invention is to be applied, is available as mixed carbolic acid obtained from distillation of tar, an oil component produced upon coal gasification, an acid oil component removed in the course of petroleum refining, a methylation reaction product of cresol, or a distillation fraction thereof.

On the other hand, 1,1-di(4-hydroxyphenyl)cyclohexane which is used as a host compound in the process of the present invention is industrially produced from cyclohexane and phenol and is readily available. Details of its production process are disclosed, for example, in JP 62-263135. This compound is in the form of white solid crystals at room temperature and has a melting point of 175° C. or higher.

The feed mixture to which the present invention is applied may be a mixture containing two or more xylenol isomers or a mixture containing a single xylenol isomer and at least one non-xylenol organic substance. The method of the present invention is more useful for the former mixture.

Accordingly, the feed mixture to which the method of the present invention can be applied may be considered to contain, in addition to at least one xylenol isomer, at least one organic substance other than the specific xylenol isomer. Examples of the other organic substance can include other phenols such as other xylenol isomers, phenol, cresol and ethylphenol; neutral oils such as naphthalene and methylnaphthalene; and other impurities. The total concentration of such other organic substances may be generally 50 wt. % or lower, preferably 25 wt. % or lower, notably 10 wt. % or lower.

Xylenol includes six isomers. Of these, 2,4-xylenol and 2,5-xylenol can be hardly separated from each other by distillation especially for the closeness of their boiling points. As the method of the present invention is useful especially for a mixture one or more components of which can be hardly separated from the remaining components by the conventional methods as described above, the method of the present invention will hereinafter be described in further detail by taking a mixture of 2,4-xylenol and 2,5-xylenol as a typical example.

Where a feed mixture is a mixture containing both 2,4-xylenol and 2,5-xylenol, the concentration of 2,4-xylenol in the mixture may amount generally to more than 75 mole %, preferably 80 mole % or higher of the whole xylenol when separation and purification of 2,4-xylenol is intended. When separation and purification of 2,5-xylenol is intended, on the other hand, the concentration of 2,5-xylenol in the mixture may amount generally to 25 mole t or higher, preferably 50 mole % or higher, notably 80 mole % or higher of the whole xylenol.

Where a large majority of a feed mixture is composed of 2,4-xylenol and 2,5-xylenol, 2,4-xylenol is selectively included and separated by a host compound when the concentration of 2,4-xylenol is higher than that of 2,4-xylenol in a composition in which 2,4-xylenol amounts to about 75 mole % of the whole xylenol and 2,5-xylenol amounts to about 25 mole % of the whole xylenol. When the concentration of 2,5-xylenol is higher than about 25 mole %, on the other hand, 2,5-xylenol is selectively included and separated by the host compound. This reversal in selectivity acutely takes place depending on the proportions of 2,4-xylenol and 2,5-xylenol, so that the method of the present invention is effective especially for separating and purifying 2,4-xylenol and 2,5-xylenol from each other from a mixture containing both of the xylenol isomers.

Since 2,5-xylenol can be included and separated with good selectivity by the host compound even when the concentration of 2,5-xylenol in the feed mixture is relatively low, for example, 25 to 60 wt. % or so, the method of the present invention is especially effective for the separation and purification of 2,5-xylenol.

To form the complex from the xylenol and the host compound in the method of this invention, the mixture of the xylenol isomers, as a feed, and the host compound are mixed and heated into a uniform solution, followed by cooling so that the resultant complex is caused to precipitate. With a view to adjusting the shape of crystals of the complex and the rate of their formation and also to facilitating recovering procedures for the complex, it is preferable to conduct the formation of this complex in the presence of a solvent. Where no solvent is required particularly as in such a case that the feed mixture is liquid or the feed mixture is heated and melted, the formation of the complex can be conducted in a solventless manner.

Preferred as the solvent for use upon formation of the complex is a solvent which well dissolves feed components still remaining without being included and separated by the host compound and which dissolves the host compound while being hot but does not dissolve the host compound while being cold. Illustrative are ethers such as diethyl ether, tetrahydrofuran and dioxane; esters such as methyl acetate and ethyl acetate; ketones such as acetone, butanone and methyl isobutyl ketone; halogenated hydrocarbons such as dichloromethane, chloroform and 1,2-dichloroethane; aliphatic hydrocarbons such as pentane, hexane, octane, decane and cyclohexane; aromatic hydrocarbons such as benzene, toluene, xylene and mesitylene; and mixtures thereof. These solvents can be used in desired amounts. It is however desired to use them generally in an range of from about 1 to 100 parts by weight per 100 parts by weight of the feed mixture.

No particular limitation is imposed on the mixing proportions of the host compound and the feed mixture upon formation of the complex. If the proportion of the feed mixture is extremely high, the proportion of separated xylenol isomer becomes small relative to the feed mixture subjected to the separation. The separation and purification method is therefore inefficient. If the proportion of the host compound is extremely high, the proportion of separated xylenol isomer becomes small relative to the host compound employed. The separation and purification method is therefore in-efficient and moreover, the selectivity of inclusion is reduced. It is therefore not preferred to use the feed mixture and the host compound at an unduly high or low ratio. The suitable mixing proportion of the host compound may range from 0.05 to 10 moles, preferably from 0.2 to 2 moles per mole of the xylenol isomer to be separated.

Upon formation of the complex in the present invention, the feed mixture and the host compound are mixed and heated into a solution. No particular problem arises with respect to the heating temperature insofar as it is in such a range as making it possible to form the mixture into a uniform solution without substantial evaporation of the xylenol isomer to be separated or the host compound. Suitably, this heating temperature may generally be in a range of from 40 to 200° C., with a range of from 80 to 160° C. being preferred. On the other hand, the temperature at which the complex is caused to precipitate upon formation of the complex varies depending on conditions such as the feed mixture and solvent used. In general, however, this precipitation may be effected at room temperature. To increase the amount of the complex to be recovered, however, this temperature may be set at a level lower than room temperature by cooling such as forced cooling or a cooling medium as needed. For the simplification of the step, the temperature may also be set at a level higher than room temperature insofar as the complex can be recovered in a sufficient amount. Upon formation of the complex, the operation pressure may usually be atmospheric pressure. Depending on the boiling point of the solvent used, however, the operation may be conducted under elevated pressure or reduced pressure.

Upon formation of the complex, the atmosphere is required to be inert to such an extent as not impairing the quality of the feed mixture, host compound or solvent used and that of the xylenol isomer to be recovered. In general, an air atmosphere is acceptable. An inert gas atmosphere such as nitrogen, carbon dioxide, argon or helium may however be employed as needed. The time which is needed for the formation of the complex differs depending on the scale at which the method is to be practiced and also on the apparatus, heating conditions, cooling conditions and the like to be used. Nonetheless, this time may range approximately from 10 minutes to 48 hours or so.

Besides the procedures described above, the formation of the complex can also be practiced in various ways, including, for example, precipitation of the complex by removing a portion of a solvent by distillation or the like subsequent to dissolution of the feed mixture and the host compound in the solvent, precipitation of the complex by conducting cooling subsequent to dissolution of the feed mixture and host compound in a solvent, precipitation of the complex by adding a poor solvent subsequent to dissolution of the feed mixture and host compound in a good solvent, precipitation of the complex by removing a good solvent by distillation subsequent to dissolution of the feed mixture and host compound in a mixture of the good solvent and a poor solvent, and where the feed mixture is liquid, precipitation of the complex by conducting cooling or adding a poor solvent subsequent to dissolution of the host compound in the feed mixture.

To perform solid-liquid separation of the complex precipitated in accordance with the method of the present invention, filtration or decantation can be relied upon. A commonly-employed procedure can be employed such as gravitational filtration, suction filtration, centrifugal filtration, filter press, screw press, centrifugation, or centrifugal decantation. Subsequent to the separation, the thus-collected complex may desirably be subjected to washing with a solvent as needed so that any components of the feed mixture, said components still remaining without inclusion and separation, can be removed to improve the quality of the recovered xylenol isomer. As the washing solvent, it is possible to use the same solvent as that employed upon formation of the complex. The atmosphere for the solid-liquid separation can be an air atmosphere in general. It can also be an inert gas atmosphere such as nitrogen, carbon dioxide, argon or helium as needed.

For the recovery of the specific xylenol isomer from the complex containing the same in the method of the present invention, it is simple and convenient to heat and decompose the complex so that the xylenol isomer contained therein is evaporated and recovered. It is desired to conduct this thermal decomposition for the recovery of the xylenol isomer in a temperature range such that the complex is decomposed to release the xylenol isomer without occurrence of thermal decomposition of the host compound. A suitable temperature range is generally from 100 to 250° C., preferably from 150 to 200° C.

By conducting this thermal decomposition of the complex under suitable conditions for the recovery of the xylenol isomer, the released xylenol isomer can be distilled and recovered concurrently with the thermal decomposition of the complex. On the other hand, 1,1-di(4-hydroxyphenyl)cyclohexane as the host compound can be recovered as a thermal decomposition residue subsequent to the recovery of the xylenol isomer, and can then be used again without conducting purification specifically.

As procedures for recovering the xylenol isomer from the complex, it may be mentioned to add a compound, which can form a complex with the host compound more easily than the xylenol isomer, as a releasing agent for the xylenol isomer, to replace the xylenol isomer, which is included as the guest in the complex, by the releasing agent to transfer the xylenol isomer into the liquid phase, to remove the complex of the releasing agent and the host compound by solid-liquid separation, and then to recover the xylenol isomer from the filtrate.

Examples of the releasing agent to be added can include alcohols such as methanol, ethanol, n-propanol, i-propanol, n-butanol, sec-butanol, i-butanol and t-butanol; and nitriles such as acetonitrile, propionitrile and benzonitrile. These releasing agents can be used after diluting them with the same solvent as that employed upon formation of the complex.

The replacement of the xylenol isomer in the complex by the releasing agent can be effected by washing the complex, which contains the xylenol isomer as the guest, with the releasing agent or a solution thereof and then conducting filtration. The washing may be conducted under mechanical stirring, or may be performed by rinsing while holding the complex standstill. As an alternative, recrystallization of the complex in the releasing agent or a solution thereof also makes it possible to replace the xylenol isomer in the complex by the releasing agent so that the xylenol isomer is released.

Where the recovery of the xylenol isomer is conducted with this releasing agent, the host compound is recovered as a [releasing agent/host compound] complex with the releasing agent contained as a guest. The host compound can be regenerated by decomposing the complex under heat to have the releasing agent released. Where a compound of a low boiling point is used as a releasing agent, the releasing agent is released from the complex and is then distilled off when heating is conducted sufficiently upon formation of the complex between the releasing agent and the host compound. The host compound can therefore be regenerated without conducting regeneration procedures specifically.

The present invention will next be described more specifically on the basis of examples, in which designations of "%" are on a weight basis unless otherwise specifically indicated.

EXAMPLE 1

Mixed were 1.0 g of 1,1-di(4-hydroxyphenyl)cyclohexane, 1.0 g of mixed xylenol consisting of 10.7% of 2,4-xylenol, 85.8% of 2,5-xylenol and 3.5% of others, and 20 g of mesitylene as a solvent. The resulting mixture was heated to 150° C., whereby a uniform solution was obtained. This solution was left over at room temperature for 6 hours so that a complex was allowed to precipitate. The precipitate was collected by suction filtration, thoroughly washed with toluene and hexane, and then dried in air, whereby 1.38 g of the complex were obtained. Upon heating this complex at 200° C. and 20 torr, 0.34 g of xylenol was recovered. The composition of the recovered xylenol was analyzed by gas chromatography. 2,5-Xylenol was found to account for 99.5% or more, and 2,4-xylenol was not detected.

EXAMPLE 2

Mixed were 1.0 g of 1,1-di(4-hydroxyphenyl)cyclohexane and 1.0 g of the same mixed xylenol as that employed in Example 1. The resulting mixture was heated to 160° C., at which the mixture was fused into a homogeneous phase. This mixture was left over at room temperature for 6 hours so that the mixture was allowed to turn into a solid. After the thus-obtained solid was thoroughly washed with toluene, the solid was collected by suction filtration, washed with hexane and then dried in air, whereby 1.38 g of a complex were obtained. When the complex was heated at 200° C. and 20 torr, 0.33 g of xylenol was recovered. The composition of the recovered xylenol was analyzed by gas chromatography. 2,5-Xylenol was found to account for 99.5% or more, and 2,4-xylenol was not detected.

EXAMPLES 3–6

Experiments were conducted under similar conditions of feed material, solvent and operation as in Example 1 except that the amount of the mixed xylenol used was changed. The experimental conditions and results are presented in Table 1, in which "2,4-isomer" indicates 2,4-xylenol while "2,5-isomer" represents 2,5-xylenol. Table 1 also shows the experimental conditions and results of Example 1.

TABLE 1

Experimental Conditions and Results (Example 1, Examples 3–6)

| | Charged | | Recovered | | | |
|---|---|---|---|---|---|---|
| | Host compound | Mixed xylenol | Amount of complex | Recovered xylenol | Comp'n of recovered xylenol (%) | |
| | (g) | (g) | (g) | (g) | 2,4-isomer | 2,5-isomer |
| Ex. 1 | 1.0 | 1.0 | 1.38 | 0.34 | Not detected | ≧99.5 |
| Ex. 3 | 1.0 | 0.5 | 1.25 | 0.21 | Not detected | ≧99.5 |
| Ex. 4 | 1.0 | 2.0 | 1.47 | 0.42 | Not detected | ≧99.5 |
| Ex. 5 | 1.0 | 3.0 | 1.49 | 0.43 | Not detected | ≧99.5 |
| Ex. 6 | 1.0 | 4.0 | 1.48 | 0.42 | Not detected | ≧99.5 |

EXAMPLE 7

Mixed were 1.0 g of 1,1-di(4-hydroxyphenyl)cyclohexane, 1.0 g of mixed xylenol consisting of 88.1% of 2,4-xylenol, 9.8% of 2,5-xylenol and 2.1% of others, and 20 g of decane as a solvent. The resulting mixture was heated to 150° C., whereby a uniform solution was obtained. This solution was left over at room temperature for 6 hours so that a complex was allowed to precipitate. The precipitate was collected by suction filtration, thoroughly washed with hexane, and then dried in air, whereby 1.37 g of the complex were obtained. When this complex was heated at 200° C. and 20 torr, 0.32 g of xylenol was recovered. The composition of the recovered xylenol was analyzed by gas chromatography. 2,4-Xylenol was found to account for 99.1% or more, and 2,5-xylenol was found to amount to 0.7%.

EXAMPLE 8

An experiment was conducted under the same conditions and in the same manner as in Example 7 except that the mixed xylenol used as the feed was replaced by mixed xylenol consisting of 78.5% of 2,4-xylenol, 19.6% of 2,5-xylenol and 1.9% of others. As a result, 1.18 g of a complex were obtained. This complex was processed in the same manner as in Example 7, whereby 0.12 g of xylenol was recovered. The contents of 2,4-xylenol and 2,5-xylenol were found to be 95.1% and 4.7%, respectively.

EXAMPLE 9

Mixed were 1.0 g of 1,1-di(4-hydroxyphenyl)cyclohexane, 1.0 g of mixed xylenol consisting of 68.7% of 2,4-xylenol, 29.4% of 2,5-xylenol and 1.9% of others, and 20 g of mesitylene as a solvent. The resulting mixture was heated to 150° C., whereby a uniform solution was obtained. This solution was left over at room temperature for 6 hours so that a complex was allowed to precipitate. The precipitate was collected by suction filtration, thoroughly washed with toluene and hexane, and then dried in air, whereby 1.28 g of the complex were obtained. When this complex was processed in the same manner as in Example 7, 0.23 g of xylenol was recovered. The contents of 2,4-xylenol and 2,5-xylenol were found to be 5.5% and 94.3%, respectively.

EXAMPLES 10–15

Experiments were conducted under the same conditions and in the same manner as in Example 9 except that the mixed xylenol employed as the feed was replaced by those having various compositions, respectively. The experimental conditions and results are presented in Table 2, in which "Xy" stands for xylenol, "2,4-isomer" indicates 2,4-xylenol, and "2,5-isomer" represents 2,5-xylenol. Further, a relationship between the contents of 2,5-xylenol in the mixed xylenols employed in Example 7–15 and the compositions of xylenols recovered there is diagrammatically shown in FIG. 1.

TABLE 2

Experimental Conditions and Results (Examples 7–15)

| | Charged Composition of mixed Xy (%) | | | Amount of complex | Amount of recovered | Comp'n of recovered Xy (%) | |
|---|---|---|---|---|---|---|---|
| | 2,4-isomer | 2,5-isomer | Others | (g) | Xy (g) | 2,4-isomer | 2,5-isomer |
| Ex. 7 | 88.1 | 9.8 | 2.1 | 1.37 | 0.32 | 99.1 | 0.7 |
| Ex. 8 | 78.5 | 19.6 | 1.9 | 1.18 | 0.12 | 95.1 | 4.7 |
| Ex. 9 | 68.7 | 29.4 | 1.9 | 1.28 | 0.23 | 5.5 | 94.3 |
| Ex. 10 | 59.0 | 39.3 | 1.7 | 1.43 | 0.38 | 2.4 | 97.4 |
| Ex. 11 | 49.3 | 49.2 | 1.5 | 1.48 | 0.41 | 2.7 | 97.2 |
| Ex. 12 | 39.4 | 59.0 | 1.6 | 1.49 | 0.43 | 1.1 | 98.7 |
| Ex. 13 | 29.6 | 69.0 | 1.4 | 1.49 | 0.43 | 1.5 | 98.3 |
| Ex. 14 | 19.7 | 79.1 | 1.2 | 1.48 | 0.44 | 0.8 | 99.1 |
| Ex. 15 | 9.9 | 88.9 | 1.2 | 1.50 | 0.44 | Not detected | ≧99.5 |

EXAMPLE 16

Mixed were 1.0 g of 1,1-di(4-hydroxyphenyl)cyclohexane, 1.0 g of mixed xylenol consisting of 49.2% of 2,3-xylenol, 49.6% of 2,4-xylenol and 1.2% of others, and 20 g of decane as a solvent. The resulting mixture was heated to 150° C., whereby a uniform solution was obtained. This solution was left over at room temperature for 6 hours so that a complex was allowed to precipitate. The precipitate was collected by suction filtration, thoroughly washed with hexane, and then dried in air, whereby 1.11 g of the complex were obtained. When this complex was heated at 200° C.

TABLE 3

Experimental Conditions and Results (Example 11, Examples 16–29)

| | Charged Composition of mixed Xy (%) | | | Amount of complex (g) | Amount of recovered Xy (g) | Comp'n of recovered Xy (%) | |
|---|---|---|---|---|---|---|---|
| Ex. 11 | 2,4-isomer 49.3 | 2,5-isomer 49.3 | Others 1.5 | 1.48 | 0.41 | 2,4-isomer 2.7 | 2,5-isomer 97.2 |
| Ex. 16 | 2,3-isomer 49.2 | 2,4-isomer 49.6 | Others 1.2 | 1.11 | 0.11 | 2,3-isomer 87 | 2,4-isomer 13 |
| Ex. 17 | 2,4-isomer 49.8 | 2,6-isomer 49.3 | Others 0.9 | 1.28 | 0.25 | 2,4-isomer 64 | 2,6-isomer 36 |
| Ex. 18 | 2,4-isomer 49.1 | 3,4-isomer 49.2 | Others 1.7 | 1.08 | 0.07 | 2,4-isomer 10 | 3,4-isomer 90 |
| Ex. 19 | 2,4-isomer 49.3 | 3,5-isomer 49.5 | Others 1.2 | 1.42 | 0.42 | 2,4-isomer 3 | 3,5-isomer 97 |
| Ex. 20 | 2,5-isomer 49.1 | 3,5-isomer 49.4 | Others 1.5 | 1.52 | 0.51 | 2,5-isomer 0.6 | 3,5-isomer 99.4 |
| Ex. 21 | 2,6-isomer 49.2 | 3,4-isomer 49.1 | Others 1.7 | 1.39 | 0.38 | 2,6-isomer 21 | 3,4-isomer 79 |
| Ex. 22 | 2,6-isomer 49.3 | 3,5-isomer 49.2 | Others 1.5 | 1.58 | 0.58 | 2,6-isomer 0.8 | 3,5-isomer 99.2 |
| Ex. 23 | 3,4-isomer 49.6 | 3,5-isomer 49.5 | Others 0.9 | 1.54 | 0.54 | 3,4-isomer 97 | 3,5-isomer 3 |
| Ex. 24 | 2,3-isomer 49.3 | 2,5-isomer 49.1 | Others 1.6 | 1.06 | 0.05 | 2,3-isomer 83 | 2,5-isomer 17 |
| Ex. 25 | 2,3-isomer 49.5 | 3,5-isomer 49.2 | Others 1.3 | 1.19 | 0.17 | 2,3-isomer 15 | 3,5-isomer 85 |
| Ex. 26 | 2,3-isomer 49.5 | 2,6-isomer 49.3 | Others 1.2 | 1.31 | 0.32 | 2,3-isomer 97 | 2,6-isomer 3 |
| Ex. 27 | 2,3-isomer 49.7 | 3,4-isomer 49.5 | Others 0.8 | 1.24 | 0.23 | 2,3-isomer 9 | 3,4-isomer 91 |
| Ex. 28 | 2,5-isomer 49.8 | 2,6-isomer 49.1 | Others 1.1 | 1.36 | 0.35 | 2,5-isomer 64 | 2,6-isomer 36 |
| Ex. 29 | 2,5-isomer 49.6 | 3,4-isomer 49.5 | Others 0.9 | 1.41 | 0.39 | 2,5-isomer 0.6 | 3,4-isomer 99.4 | and 20 torr, 0.11 g of xylenol was recovered. The composition of the recovered xylenol was analyzed by gas chromatography. 2,3-Xylenol was found to account for 87%, and 2,4-xylenol was found to amount to 13%.

EXAMPLES 17–23

Experiments were conducted under the same conditions and in the same manner as in Example 16 except that mixed xylenols employed as feeds were each formulated by mixing xylenol isomers at about 1:1 as in Example 11, the kinds of the isomers so mixed were changed in various ways, and decane was used as a solvent in place of mesitylene. The experimental conditions and results are presented in Table 3. The results of Example 11 and Example 16 are shown in Table 3. In the table, "Xy" stands for xylenol, while "2,3-isomer" represents 2,3-xylenol, "2,4-isomer" 2,4-xylenol, "2,5-isomer" 2,5-xylenol, "2,6-isomer" 2,6-xylenol, "3,4-isomer" 3,4-xylenol, "3,5-isomer" 3,5-xylenol.

EXAMPLES 24–29

Experiments were conducted under the same conditions and in the same manner as in Example 16 except that mixed xylenols employed as feeds were each formulated by mixing xylenol isomers at about 1:1 as in Example 11 and the kinds of the isomers so mixed were changed in various ways. The experimental conditions and results are presented in Table 3. In the table, "Xy" stands for xylenol, while "2,3-isomer" represents 2,3-xylenol, "2,4-isomer" 2,4-xylenol, "2,5-isomer" 2,5-xylenol, "2,6-isomer" 2,6-xylenol, "3,4-isomer" 3,4-xylenol, "13,5-isomer" 3,5-xylenol.

EXAMPLE 30

Mixed were 100.4 g of 1,1-di(4-hydroxyphenyl)cyclohexane, 101.4 g of mixed xylenol consisting of 10.7% of 2,4-xylenol, 85.8% of 2,5-xylenol and 3.5% of others as in Example 1, and 400 g of mesitylene as a solvent. In a similar manner as in Example 1, 138.8 g of a complex were obtained. A 50.1 g portion of the complex was taken, followed by the addition of 75 g of n-butanol as a releasing agent. The thus-obtained mixture was stirred for 30 minutes to replace the xylenol in the complex by the releasing agent. The mixture was then filtered under suction, and the [releasing agent/host compound] complex was thoroughly washed with hexane. The complex was dried in air, whereby 40.6 g of the [releasing agent/host compound] complex were recovered. The resultant filtrate and washing were entirely recovered, concentrated under reduced pressure, and then distilled under reduced pressure, whereby 11.5 g of xylenol were recovered. The composition of the recovered xylenol was analyzed by gas chromatography. 2,5-Xylenol was found to account for 99.5% or more, and 2,4-xylenol was not detected.

EXAMPLE 31

Mixed were a 15.0 g portion of the [releasing agent/host compound] complex recovered in Example 30, 15.0 g of the same mixed xylenol as that employed in Example 1, and 80 g of mesitylene as a solvent. The resulting mixture was heated until mesitylene boiled, whereby a uniform solution was formed. After 20 g of the solvent were distilled out, the solution was cooled, and was then left over at room temperature for 6 hours so that a complex was allowed to precipitate. By this processing, the releasing agent in the [releasing agent/host compound] complex was replaced by xylenol. By a gas chromatographic analysis, the distilled solvent was found to contain 21.5% of n-butanol. The above-obtained complex was processed in the same manner as in Example 1, whereby 15.2 g of the complex were obtained. This complex was subjected to thermal decomposition in a similar manner as in Example 1, whereby 4.3 g of xylenol were obtained. The composition of the thus-recovered xylenol was analyzed by gas chromatography. 2,5-Xylenol was found to account for 99.5% or more, and 2,4-xylenol was not detected.

EXAMPLE 32

In a 500-ml beaker, a 50.2 g portion of the complex obtained in Example 30 was placed. Into the beaker, 75 g of a 1:1 w/w mixture of i-propanol and hexane were gently added as a releasing agent. The resulting mixture was left standstill for 30 minutes to replace the xylenol in the complex by the releasing agent. The mixture was then filtered under suction, and the [releasing agent/host compound] complex was thoroughly washed with hexane. The resultant filtrate and washing were entirely recovered, concentrated under reduced pressure, and then distilled under reduced pressure, whereby 11.2 g of xylenol were recovered. The composition of the recovered xylenol was analyzed by gas chromatography. 2,5-Xylenol was found to account for 99.5% or more, and 2,4-xylenol was not detected.

The present invention has been described above primarily with respect to the separation and purification of mixtures of xylenol isomers. It is however to be noted that the present invention is not limited to the separation of such isomers but is also useful as a method for separating and purifying xylenol alone from a feed mixture which contains xylenol and at least one non-xylenol component (impurity).

This application claims the priority of Japanese Patent Application No. HEI 10-72751 filed Mar. 20, 1998, which is incorporated herein by reference.

What is claimed is:

1. A method for the separation and purification of at least one specific xylenol isomer from a mixture comprising said specific xylenol isomer and at least one organic substance other than said specific xylenol isomer, which comprises bringing said mixture into contact with 1,1-di(4-hydroxyphenyl)cyclohexane as a host compound to form a complex of said specific xylenol isomer as a guest compound with said host compound, and then having said specific xylenol isomer released from said complex.

2. A method according to claim 1, wherein said at least one other organic substance is a xylenol isomer other than said at least one xylenol isomer.

3. A method according to claim 2, wherein one of said at least one xylenol isomer and said xylenol isomer other than said at least one xylenol isomer is 2,4-xylenol, and the other is 2,5-xylenol.

4. A method according to claim 3, wherein 2,5-xylenol amounts to at least 25 mole % of whole xylenol, and 2,5-xylenol is separated and purified.

5. A method according to claim 3, wherein 2,5-xylenol amounts to less than 25 mole % of whole xylenol, and 2,4-xylenol is separated and purified.

6. A method according to claim 1, wherein said release of said xylenol isomer is conducted in a solvent.

7. A method according to claim 6, wherein said solvent dissolves said host compound while being hot but causes said host compound to precipitate while being cold.

8. A method according to claim 1, wherein said host compound is used in a range of from 0.05 to 10 moles per mole of said xylenol isomer to be separated.

9. A method according to claim 1, wherein said host compound is used in a range of from 0.2 to 2 moles per mole of said xylenol isomer to be separated.

10. A method according to claim 1, wherein said mixture is mixed carbolic acid available from distillation of tar or a distillate thereof.

* * * * *